United States Patent [19]

Nowogrodzki et al.

[11] Patent Number: 4,513,748
[45] Date of Patent: Apr. 30, 1985

[54] DUAL FREQUENCY HEART RATE MONITOR UTILIZING DOPPLER RADAR

[75] Inventors: Markus Nowogrodzki, Sussex; Daniel D. Mawhinney, Livingston, both of N.J.

[73] Assignee: RCA Corporation, Princeton, N.J.

[21] Appl. No.: 527,768

[22] Filed: Aug. 30, 1983

[51] Int. Cl.³ .............................................. A61B 5/02
[52] U.S. Cl. .................... 128/653; 128/663; 128/687; 128/661
[58] Field of Search ............. 128/653, 661, 663, 687, 128/689, 698, 721

[56] References Cited

U.S. PATENT DOCUMENTS

| | | | |
|---|---|---|---|
| 3,483,860 | 12/1969 | Namerow | 128/653 |
| 3,561,430 | 2/1971 | Filler, Jr. et al. | 128/661 |
| 3,780,726 | 12/1973 | Hatke | 128/661 |
| 4,307,728 | 12/1981 | Walton | 128/687 |
| 4,357,944 | 11/1982 | Mauser et al. | 128/663 |

FOREIGN PATENT DOCUMENTS 0749384 7/1980 U.S.S.R. .............................. 128/661

Primary Examiner—William E. Kamm
Assistant Examiner—Mitchell J. Shein
Attorney, Agent, or Firm—Joseph S. Tripoli; Robert L. Troike; Raymond E. Smiley

[57] ABSTRACT

A heart rate monitor for use where direct contact with a patient cannot be made utilizes two continuous radio frequency (RF) signals, one of relatively low frequency and one of relatively high frequency directed toward the patient whose heart is to be determined. Doppler shifted signals are reradiated by the patient back to the monitor. The reradiated low RF signal has doppler components due to bodily motion caused by respiration and heartbeat. The reradiated high RF signal has doppler components due to patient bodily movement caused by respiration. Doppler components due to heartbeat if any, are of substantially lower value than those associated with the low RF signal. The heart rate monitor includes a difference amplifier which effectively subtracts the doppler signal associated with the high RF frequency from the doppler signal associated with the low RF frequency to obtain a signal which contains only components due to the heartbeat of the patient.

9 Claims, 1 Drawing Figure

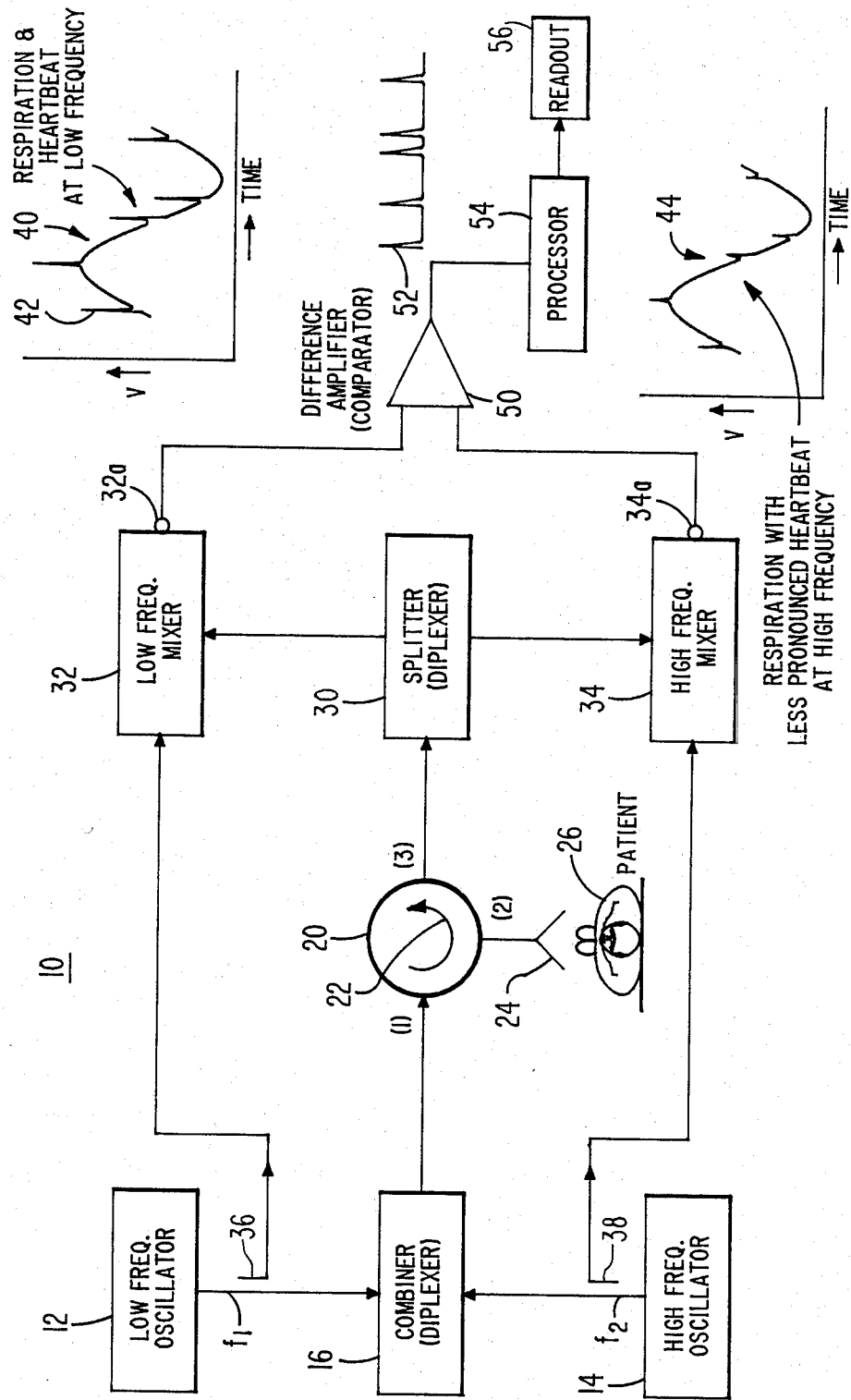

DUAL FREQUENCY HEART RATE MONITOR UTILIZING DOPPLER RADAR

This invention is concerned with measurement of patent heart rate and more particularly with such measurement where the measurement equipment cannot come in contact with the patient's body.

BACKGROUND OF THE INVENTION

Many systems are known for measuring the heart rate of a person. Such systems require that the patient be undressed in the area of a pulse point, or at least be lightly clad thereat. In some military situations or emergency situations a person becomes injured such that a heart rate measurement is desired while the person is wearing heavy protective clothing that cannot easily or quickly be removed. An example of where such a situation arises is in firefighting.

It is well known that continuous wave (cw) microwave radar, commonly referred to as doppler radar, can be used to sense and measure motion. Basically, the operation of cw microwave radar can be understood by considering the consequence of combining, or mixing, a sample of the transmitted signal with the miniscule amount of signal reflected back from some object, commonly referred to as the target. Depending upon the phase relations between the sample and the reflected signals, the result will be usually a minute increase or decrease in the detectable signal level at this point. Except in specialized interferometer type measurement apparatus where it may be used to determine position, this fixed offset level is barely discrenible and not expecially useful.

If, however, the target is in motion relative to the transmitter, then the small offset level changes and a small time-varying component, often called the doppler signal, is added to the mixed signal. It is this alternating signal that is processed in most simple cw microwave radars.

For speedometers or traffic control radars, the frequency of the alternating signal, the doppler frequency, is proportional to relative speed and is processed to display miles per hour. For motion detectors, such as automatic door openers, the presence of an alternating signal is sufficient to trigger the desired response.

For measuring the periodicity of some form of regular reciprocating motion, the waveform obtained from the detected mixer output can be filtered and viewed on an oscillograph or processed and counted against a known timebase to compute revolutions per minute or, as in the area of interest of this invention heartbeats per minute.

It is possible to use doppler type radar to detect the movement of the heart if the patient can stay still and stop breathing while the measurement is being taken. However, a patient that can exercise that much control over his physical movement probably doesn't have to have his heart rate determined while wearing protective clothing.

It is a known fact that higher microwave frequencies do not penetrate human tissues as well as lower frequencies. This fact is utilized in the instant invention.

SUMMARY OF THE INVENTION

In accordance with a preferred embodiment of the present invention a heart rate monitor comprises in combination first means for producing a first radio frequency (RF) signal at a first relatively low frequency and for producing a second RF signal at a second relatively high frequency, second means adapted for directing the first and second RF signals toward a patient whose heart rate is to be determined and for receiving back therefrom doppler shifted signals at the two RF frequencies, means for removing respective RF frequencies from the return signals thereby leaving the doppler signal components thereof. The doppler signal associated with both RF signals contains signal components of the same values associated with patient movement due to respiration, while the doppler signal associated with the higher RF frequency contains components associated with patient movement due to heart rate. The heart rate monitor also includes means for combining the two doppler signals to suppress those portions corresponding with respiration thus leaving that portion associated with heart rate.

BRIEF DESCRIPTION OF THE DRAWING

The sole FIGURE is a heart rate monitor in accordance with a preferred embodiment of the present invention.

DETAILED DESCRIPTION

In the sole FIGURE a low frequency oscillator 12 and a high frequency oscillator 14 may each be adapted to produce RF continuous wave signals at frequencies f1 and f2, respectively. A typical frequency f1 for low frequency oscillator 12 may be 1 GHz. A typical frequency f2 for high frequency oscillator 14 may be 10 GHz. A typical range of frequencies is 0.9 GHz to 20 GHz and typically f2=10·f1.

Oscillators 12 and 14 are coupled to a combiner circuit 16 which by way of example may be a diplexer of the type made by Wavecom as Model M-205-1. Combiner 16 produces a composite signal containing components at frequencies f1 and f2 which composite signal is applied to one port arbitrarily legended (1) of a three-port circulator 20. Signal transmission in circulator 20 is in the direction of arrow 22. Port (2) of circulator 20 is coupled to a bidirectional antenna 24 for radiating, to a patient 26, RF frequencies f1 and f2 and for receiving back therefrom a reradiated doppler shifted signal.

The doppler shift is due to patient movement. The patient movement is due to two causes—1. respiration and other bodily movements such as arm and leg movements and thrashing about and 2. heartbeat. The effects on the reradiated signal due to the two types of motion will be discussed in more detail hereinafter.

Port (3) of circulator 20 is coupled to splitter circuit 30 which may also be a diplexer by way of example, to pass reradiated signals from patient 26 thereto. Splitter 30 splits the signal transmitting the part associated with frequency f1 to low frequency mixer 32 and transmitting the part associated with frequency f2 to high frequency mixer 34.

A coupler 36 is also coupled to low frequency mixer 32. Coupler 36 couples a sample of frequency f1 to mixer 32 which subtractively mixes f1 with the doppler shifted signal at f1 as received from splitter 30 to remove the carrier frequency f1 leaving only the doppler signal at mixer output terminal 32a. Similarly, coupler 38 is also coupled to high frequency mixer 34. Coupler 38 couples a sample of frequency f2 to mixer 34 which subtractively mixes f2 with the doppler shifted signal at frequency f2 as received from splitter 30 to remove the carrier frequency f2 leaving only the doppler signal at mixer output terminal 34a. The output signal at terminal 32a is illustrated in waveform 40 which is plotted as voltage on the vertical axis vs. time on the horizontal axis. The component of signal substantially in the shape of a sinewave is due to respiration. The spikes such as 42 are heartbeat pulses.

The output signal at terminal 34a is illustrated in waveform 44 which is also plotted as voltage on the vertical axis vs. time on the horizontal axis. As with waveform 40 the component of signal in the shape of a sinewave is due to respiration. The amplitude and frequency of the sinewave signals in waveforms 40 and 44 are identical. It will be noted that waveform 44 contains at most only small amplitude spikes due to heartbeat. It was mentioned earlier that low frequency signals such as for example at 1 GHz tend to penetrate more deeply into the human body and therefore will pick up motion due to heartbeat. Conversely, higher frequency signals such as at 10 GHz tend not to penetrate into the human body and therefore will pick up only surface motion such as that due to respiration and actual physical movements of different parts of the body. Therefore, it follows that waveform 44 does not contain a strong component due to the heart motion since the heart is burried inside the human body.

Terminals 32a and 34a are connected to respective inputs of a difference amplifier 50. Difference amplifier 50 essentially subtracts waveform 44 from waveform 40 thus eliminating those portions of the waveform due to respiration and other physical movement of bodily limbs leaving only that portion of the signal due to the heartbeat that is that portion of the signal corresponding to spikes such as 42 in waveform 40. The resulting signal as illustrated at waveform 52 may be viewed at the output of amplifier 50. Alternatively or additionally, the output of amplifier 50 may be coupled to a processor circuit 54 which may produce a number which corresponds to the heart rate of the patient as displayed at readout 56.

In operation antenna 24 is positioned in proximity to the heart (not shown) of a patient 26 whose heart rate is to be measured. The presence of heavy protective clothing will not interfere with the operation of heart rate monitor 10. Oscillators 12 and 14 are made operational such that frequencies f1 and f2 are directed by antenna 24 toward patient 26. Doppler motion of the patient due to respiration, limb movements and heartbeat cause doppler shifts in the frequencies f1 and f2 less the heartbeat component and the doppler shifted signals are reradiated via antanna 34 to splitter 30 and thence to mixers 32 and 34. Those mixers remove the respective carrier frequencies f1 and f2 leaving only doppler signals at output terminals 32a and 34a. As mentioned previously the signal produced at output terminal 32a because it is due to a low frequency carrier f1 will contain components corresponding to heartbeat. In contrast, the output signal at terminal 34a being due to a high frequency carrier signal contains no or very reduced signals due to heartbeat. Difference amplifier 50 creates a signal corresponding to the difference between amplifiers produced by mixers 32 and 34 which emphasizes the signal due to heartbeat and deemphasizes or removes the signal due to respiration and movement of other limbs of patient 26.

What is claimed is:

1. A heart rate monitor comprising in combination:
   first means for producing a first radio frequency (RF) signal at a relatively low frequency and for producing a second RF signal at a relatively high frequency;
   second means coupled to said first means and adapted for radiating signals therefrom toward a patient whose heart rate is to be measured and for receiving doppler shifted signals back from said patient at the frequencies of said first and second RF signals;
   third means for removing the respective RF frequencies from the returned signals leaving the doppler signal components thereof, said doppler signal associated with both RF signals containing signal components of the same values corresponding to patient movement due to respiration, the doppler signal associated with the low RF frequency containing characteristics associated with patient movement due to heartbeat; and
   fourth means for combining the two doppler signals to remove the components thereof which are common to both signals and thereby leaving the component of signal which is associated with heartbeat, the number of heartbeats per unit time corresponding to heart rate.

2. The combination as set forth in claim 1 wherein said first means comprises a low frequency oscillator, a high frequency oscillator and a combiner circuit receptive of signals from said low frequency oscillator and said high frequency oscillator for producing a composite signal containing both frequency characteristics.

3. The combination as set forth in claim 2 wherein said third means comprises first and second mixers and a splitter connected to said second means to receive doppler shifted signals therefrom and connected as one input to each of said first and secon mixers for passing to said first mixer signal components associated with said low frequency and for passing to said second mixer frequency components associated with said high frequency, said first mixer being responsive to said low frequency as transmitted for mixing it with said low frequency component of the return signal to produce thereby said doppler component of the low frequency signal, said high frequency mixer being responsive to said relatively high frequency for mixing it with the component of said return signal which contains said high frequencies to produce said doppler components associated with said high frequency.

4. The combination as set forth in claim 3 wherein said fourth means comprises a comparator circuit.

5. The combination as set forth in claim 2 wherein said fourth means comprises a comparator circuit.

6. The combination as set forth in claim 1 wherein said first means comprises a low frequency oscillator producing frequency f1, a high frequency oscillator producing frequency f2 which is equal to about 10 f1 and a combiner circuit receptive of signals from said low frequency oscillator and said high frequency oscillator for producing a composite signal containing both frequency characteristics.

7. The combination as set forth in claim 1 wherein said third means comprises first and second mixers and a splitter connected to said second means to receive doppler shifted signals therefrom and connected as one input to each of said first and second mixers for passing to said first mixer signal components associated with said low frequency and for passing to said second mixer frequency components associated with said high frequency, said first mixer being responsive to said low frequency as transmitted for mixing it with said low frequency component of the return signal to produce thereby said doppler component of the low frequency signal, said high frequency mixer being responsive to said relatively high frequency for mixing it with the component of said return signal which contains said high frequencies to produce said doppler components associated with said high frequency.

8. The combination as set forth in claim 7 wherein said forth means comprises a comparator circuit.

9. The combination as set forth in claim 1 wherein said fourth means comprises a comparator circuit.

* * * * *